(12) United States Patent
Richardson (10) Patent No.: US 9,566,069 B2
(45) Date of Patent: Feb. 14, 2017

(54) LIGATING INSTRUMENT

(71) Applicant: Boston Scientific Scimed, Inc., Maple Grove, MN (US)

(72) Inventor: M. Kevin Richardson, Austin, TX (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/339,173

(22) Filed: Jul. 23, 2014

(65) Prior Publication Data

US 2014/0336674 A1 Nov. 13, 2014

Related U.S. Application Data

(63) Continuation of application No. 11/580,865, filed on Oct. 16, 2006, now Pat. No. 8,821,515.

(51) Int. Cl.
*A61B 17/12* (2006.01)
*A61B 17/00* (2006.01)

(52) U.S. Cl.
CPC ............ *A61B 17/12013* (2013.01); *A61B 2017/00292* (2013.01); *A61B 2017/12018* (2013.01)

(58) Field of Classification Search
CPC .............. A61B 17/12013; A61B 2017/00292; A61B 2017/12018
See application file for complete search history.

(56) References Cited

U.S. PATENT DOCUMENTS 5,968,056 A * 10/1999 Chu ............... A61B 17/12013 606/139
2004/0006256 A1 * 1/2004 Suzuki et al. ............... 600/140

* cited by examiner

*Primary Examiner* — Julie A Szpira
(74) *Attorney, Agent, or Firm* — Fay Kaplun & Marcin, LLP (57) ABSTRACT

A ligating instrument is provided, including an elongate member, such as a tube, having a lumen, the elongate member extending from a proximal actuator member to a distal ligating band dispenser. A pull line may extend through the lumen of the elongate member, with a proximal end of the pull line connected to the actuator member and a distal end of the pull line connected to the ligating band dispenser, wherein actuation of the actuator member draws the pull line in a proximal direction through the elongate member to deploy the ligating bands. The ligating band dispenser may be adapted to be mounted on the distal tip of an endoscope, and the elongate member may be adapted to be positioned outside of the endoscope from the ligating band dispenser to the actuator member. Alternatively, a ligating instrument may be provided for use with an endoscope, wherein a pull line of the ligating instrument is adapted to be positioned outside of the endoscope, wherein the pull line may be secured to the endoscope by clips or some other means. In a method of using a ligating instrument with an endoscope, a distal ligating band dispenser is attached to a distal tip of an endoscope, and a pull line of the ligating instrument is extended on the outside of the endoscope, such that the pull line extends, on the outside of the endoscope, from the distal ligating band dispenser to a proximal actuator member.

10 Claims, 6 Drawing Sheets

LIGATING INSTRUMENT

PRIORITY CLAIM

The present application is a Continuation of U.S. patent application Ser. No. 11/580,865 filed on Oct. 16, 2006; now U.S. Pat. No. 8,821,515. The entire disclosure of the above patent is expressly incorporated herein by reference.

TECHNICAL FIELD

The present invention relates to medical ligating instruments and more particularly to medical ligating instruments that dispense ligating bands.

BACKGROUND OF THE INVENTION

Ligation is a medical procedure whereby the physician ties off or mechanically constricts a piece of body tissue with an encircling ligature such as a suture, clip, or elastic band. The purpose of ligation is to impede or obstruct the flow of blood, fluids, and other bodily materials through the tissue. For example, the physician can remove target tissue by ligating it to obstruct all circulation through the target tissue, thereby causing the tissue to die and slough off.

For ligating tissue inside a body cavity, orifice, or lumen, physicians often use an endoscope to access the target tissue and ligate it. In one such form of endoscopic ligation, the physician uses the endoscope to position a stretched elastic band over the target tissue and then release the band onto the tissue so that the band contracts and catches the tissue. The inward pressure of the elastic band constricts the target tissue.

Ligating instruments have been the subject of a number of patents, including U.S. Pat. No. 5,269,789 to Chin et al.; U.S. Pat. No. 5,356,416 to Chu et al.; U.S. Pat. No. 5,398,844 to Zaslaysky et al.; U.S. Pat. No. 5,857,585 to Tolkoff et al.; U.S. Pat. No. 5,853,416 to Tolkoff; U.S. Pat. No. 5,913,865 to Fortier et al.; U.S. Pat. No. 6,235,040 to Chu et al.; and U.S. Pat. No. RE 36,629 to Zaslaysky et al. The disclosures of these prior U.S. patents are expressly incorporated by reference herein.

A number of previous ligating instruments have relied on deployment of the elastic bands by a trigger wire or string that must be threaded through the lumen of an endoscope. Once the wire or string is threaded through the endoscope lumen, the user must then tie or otherwise connect the free end of the wire or string to an actuator mechanism. The process of threading the wire or string and attaching it to the actuator mechanism adds additional steps in setting-up the instrument for use and can be cumbersome. It can also lead to error and improper calibration of the device.

SUMMARY OF THE INVENTION

In accordance with certain embodiments of the invention, a ligating instrument for deploying ligating bands is provided, wherein the ligating instrument comprises an elongate member, such as a tube, having a lumen, the elongate member extending from a proximal actuator member of the ligating instrument to a distal ligating band dispenser of the ligating instrument. In accordance with such embodiments, a pull line extends through the lumen of the elongate member, with a proximal end of the pull line connected to the actuator member and a distal end of the pull line connected to the ligating band dispenser, wherein actuation of the actuator member draws the pull line in a proximal direction through the elongate member to deploy the ligating bands.

A ligating instrument according to these embodiments may be designed such that the ligating band dispenser is adapted to be mounted on the distal tip of an endoscope. The elongate member may be adapted to be positioned outside of the endoscope from the ligating band dispenser to the actuator member. The ligating instrument may include a sleeve adapted to be extended to secure at least a portion of the elongate member relative to the outside of the endoscope. In certain embodiments, the sleeve may comprise the pull line and/or the elongate member.

In accordance with other embodiments of the invention, the ligating instrument may be free-standing such that it need not be connected to an endoscope.

In accordance with other embodiments of the invention, a ligating instrument may be provided for use with an endoscope, wherein a pull line of the ligating instrument is adapted to be positioned outside of the endoscope from a ligating band dispenser to an actuator member. The pull line may be secured to the endoscope by clips or some other means.

In accordance with other embodiments of the invention, a method of using a ligating instrument with an endoscope is provided. A distal ligating band dispenser of the ligating instrument is attached to a distal tip of an endoscope, and a pull line of the ligating instrument is extended on the outside of the endoscope, such that the pull line extends, on the outside of the endoscope, from the distal ligating band dispenser to a proximal actuator member. The ligating instrument may have an elongate member having a lumen, such that the pull line extends through the lumen of the elongate member. The method may include the step of extending a sleeve to secure at least a portion of the pull line or elongate member relative to the outside of the endoscope. The method may also include the step of attaching the actuator member to the proximal end of the endoscope.

It will be appreciated that having a ligating instrument in which a pull line is not threaded through an endoscope lumen provides for simplified set-up. It will be appreciated that, in such embodiments, it may be provided such that there is no need for the user to tie or otherwise connect a free end of the pull line to an actuator mechanism. Also, the ligating device may be provided such that no additional calibration by the user is required.

It will also be appreciated that, in certain embodiments of the invention, the ligating instrument may be provided as a single functional unit. It can be mounted on the endoscope as a single functional unit or used independently. In addition, the distal ligating band dispenser may be mounted on the distal end of an endoscope while the proximal actuator member is not mounted on the endoscope, allowing for operation of the ligating instrument remote from and/or independent from the endoscope.

DETAILED DESCRIPTION

Figure 1:
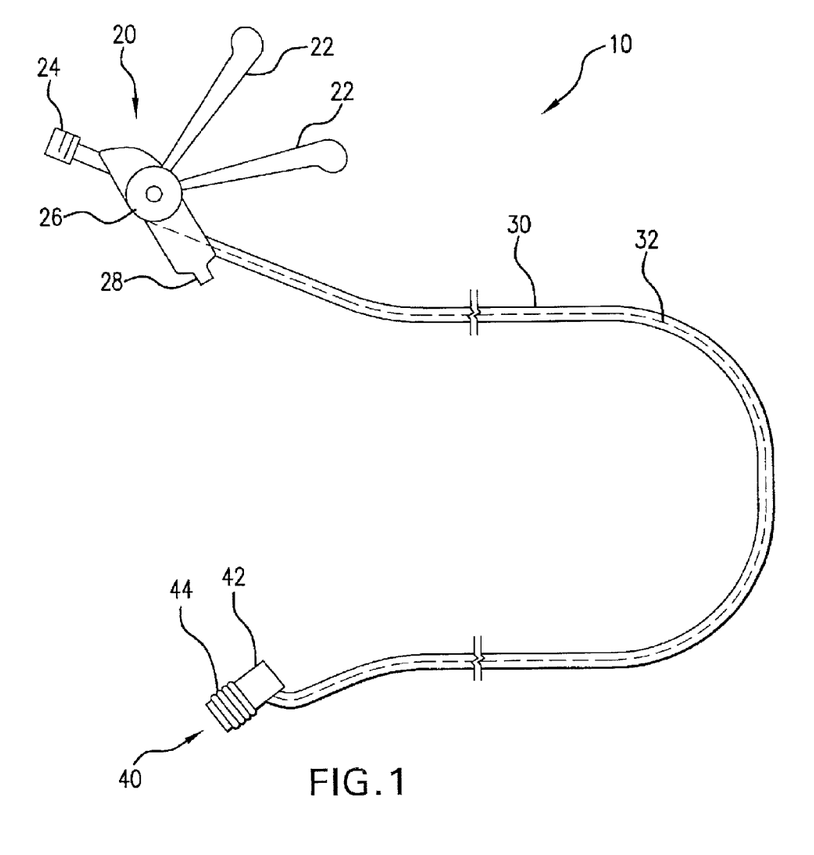
FIG. 1 is a side view of a ligating instrument in accordance with one embodiment of the present invention.

A ligating instrument 10 in accordance with one possible embodiment of the present invention is illustrated in FIG. 1. At the distal end of the instrument 10 is a ligating band dispenser 40 that dispenses ligating bands 44. In this embodiment, the ligating band dispenser 40 is adapted to be coupled to the distal tip of an endoscope 50 and includes a plurality of ligating bands 44 that are released by the drawing of a pull line 32 in the form of a wire or string.

Figure 7:
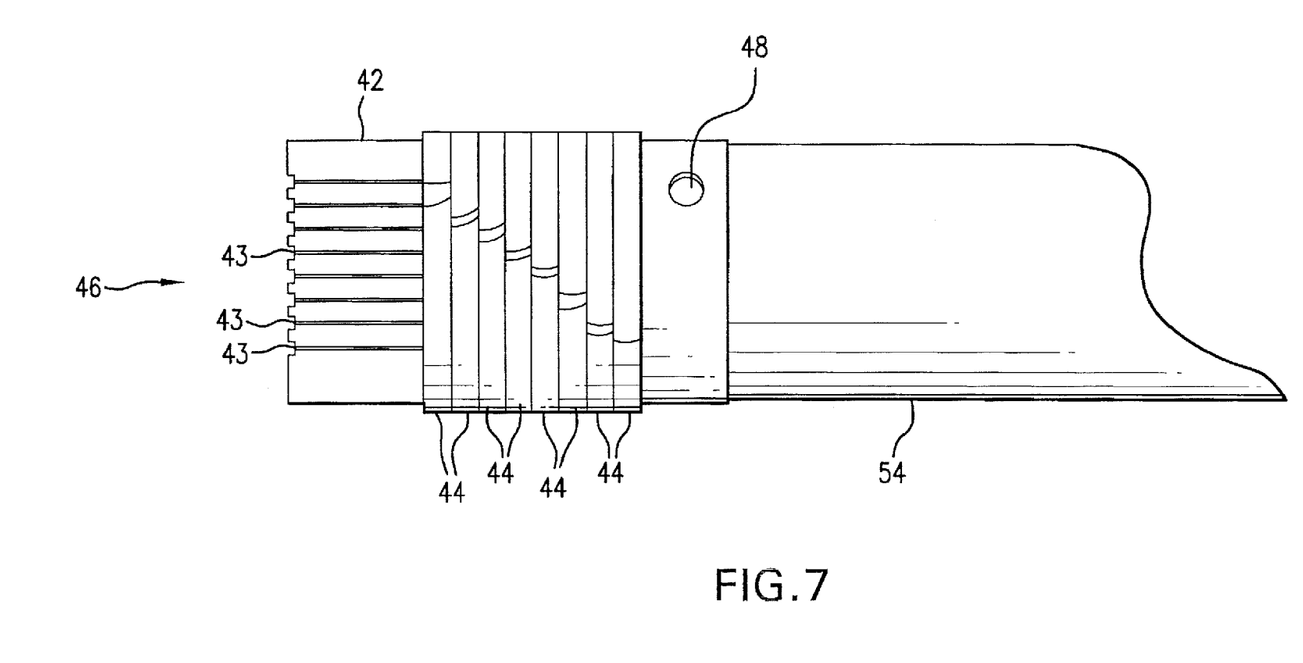
FIG. 7 is a detailed side view of a ligating band dispenser in accordance with one embodiment of the present invention.

FIG. 7 shows one possible embodiment of the ligating band dispenser 40. This embodiment of the ligating band dispenser 40 includes a support structure 42, which may be substantially cylindrical. The ligating band dispenser may be designed to be attached to the distal end of an endoscope. For example, a central bore 46 (visible in FIG. 5) in the ligating band dispenser 40 may be adapted to receive the distal tip of an endoscope tube 54.

A plurality of ligating bands 44 are received around the support structure 42. In the embodiment illustrated in FIG. 7, the pull line 32 wraps around each of the ligating bands 44, extends across the support surface 42 back and forth through a plurality of slots 43, and passes into the central bore 46. The support surface 42 may be substantially transparent, at least at a distal portion.

In accordance with embodiments of the invention, the support structure 42 may have an aperture 48 (shown in FIGS. 5 and 7) which allows the pull string to exit from the central bore 46 of the ligating band dispenser 40 to the outside of the endoscope tube 46. The aperture 48 may be positioned such that it is located distal to the distal end of the endoscope when the ligating band dispenser 40 is attached to the endoscope.

Figure 3:
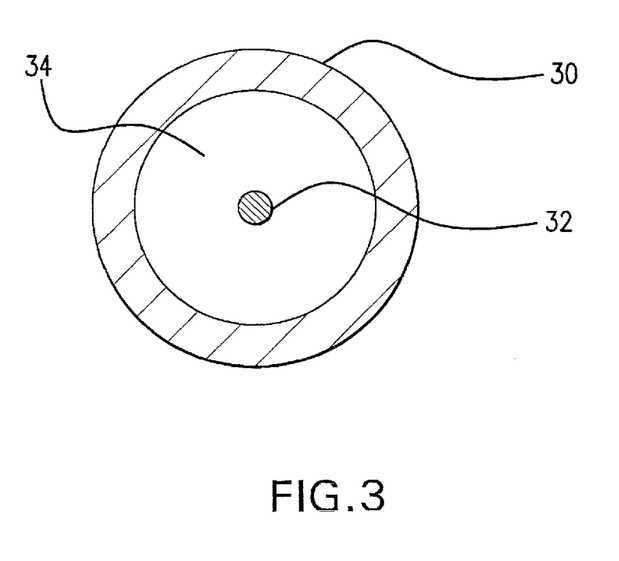
FIG. 3 is a cross-sectional view of the tubular member of FIG. 1.
Figure 4:
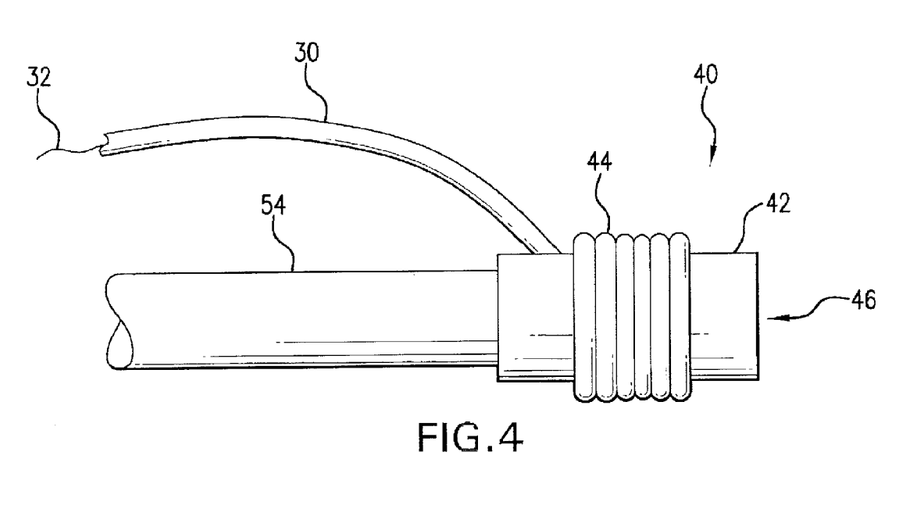
FIG. 4 is a side view of the distal end of a ligating instrument in accordance with one embodiment of the present invention.
Figure 5:
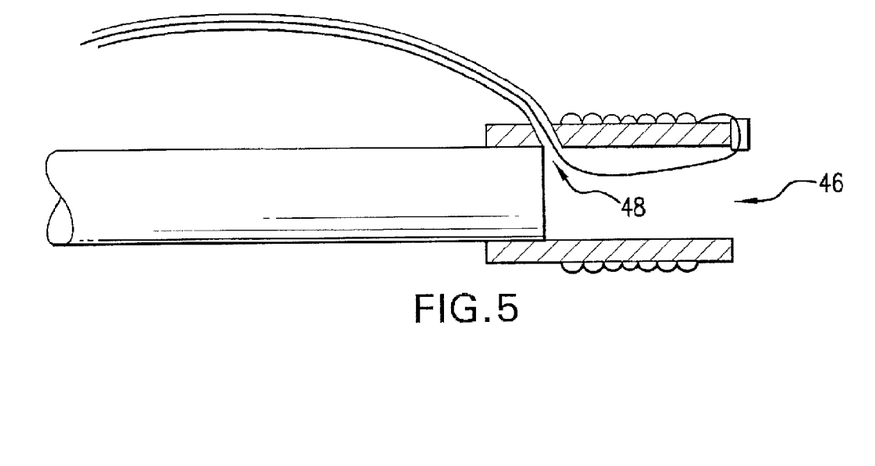
FIG. 5 is a detailed cross-sectional view of the distal end of the ligating instrument of FIG. 4.

As shown in FIGS. 4 and 5, an elongate member 30, which may be in the form of a tube, is coupled to the supporting structure 42 of the ligating band dispenser 40. The pull line 32 extends inside the lumen 34 (best shown in FIG. 3) of the elongate member 30. The pull line 32 can move freely within the lumen 34 of the elongate member 30.

Figure 6:
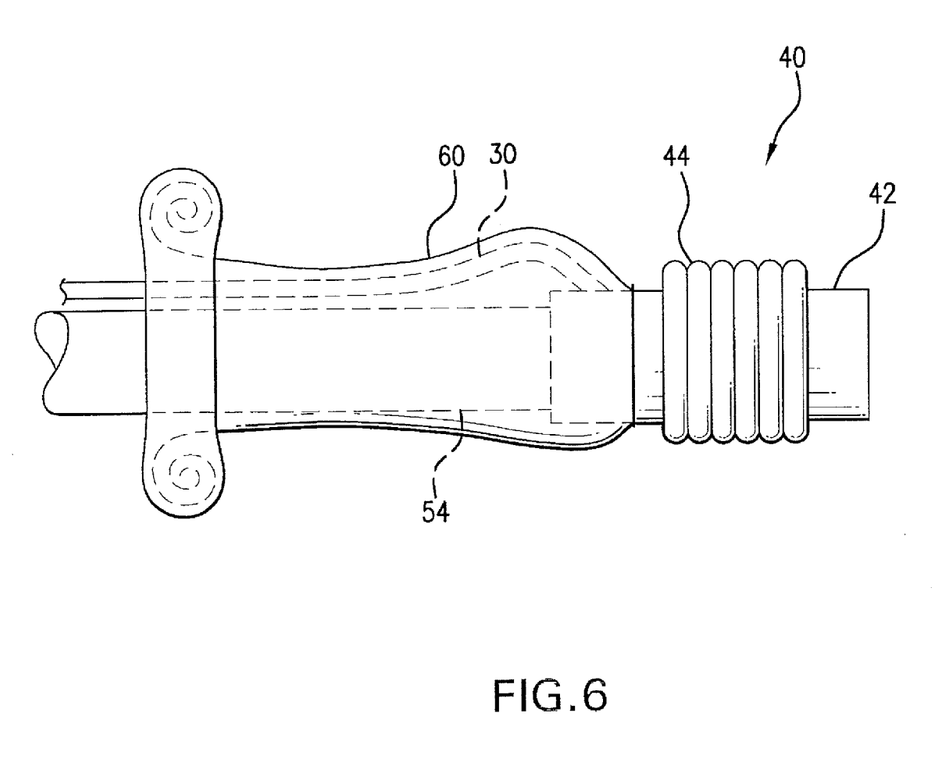
FIG. 6 is a side view of the distal end of a ligating instrument according to an alternate embodiment of the present invention, showing a sleeve covering the distal portion of the instrument and endoscope.

The elongate member 30 and pull line 32 extend alongside the endoscope tube 54 and accompany the endoscope 50 as it is inserted into a body cavity, orifice, or lumen, such as the esophagus. In one embodiment, as shown in FIG. 6, an extendable sleeve 60 is provided at a distal position on the elongate member 30, and the sleeve 60 can be extended proximally to enclose the distal portions of the elongate member 30 and endoscope tube 54. This sleeve serves to join or secure the elongate member 30, and thus the pull line 32, to the endoscope. This may aid in insertion into a body cavity, orifice, or lumen. The sleeve 60 may be made of elastomeric material and may be rolled so that it is extended by unrolling, as can be seen in FIG. 6.

In certain embodiments, the sleeve 60 may be adapted so that it comprises the elongate member 30. For example, the elongate member 30 may be incorporated into or affixed onto the sleeve 60. In some instances, the joining of the elongate member 30 and the sleeve 60 may form a single functional unit. In certain embodiments, the pull line 32 may be incorporated into the sleeve 60 such that the ligating instrument may or may not have a separate elongate member through which the pull line 32 travels. For example, the pull line 32 may travel through a channel or pathway formed within the thickness of the sleeve 60.

The elongate member 30 is sufficiently long to allow the proximal end of the elongate member 30 to exit the patient's body when the ligating band dispenser 40 is adjacent to the target site inside the body. In one embodiment, the length of the elongate member 30 may match the length of the endoscopic tube 54, but the elongate member 30 may be longer or shorter.

The proximal end of the elongate member 30 is connected to an actuator assembly 20. The pull line 32 exits the proximal end of the elongate member 30 and is connected to the actuator assembly 20. Actuation of the actuator assembly 20 operates to draw the pull line 32 in a proximal direction. The actuator assembly 20 may comprise a means for user actuation of the actuator assembly 20 to draw the pull line. The actuator assembly 20 may also comprise a means for drawing the pull line in a proximal direction. The means for drawing the pull line may also include a mechanism for preventing the pull line from moving in a distal direction. In the embodiments shown herein, the actuator assembly include a reel 26 on which the pull string is wound, and a pair of bicycle brake type of handles 22. In operation, the user squeezes the handles 22, causing a ratchet mechanism to rotate the reel 26 and draw the pull line 32 by a desired length. The ratchet mechanism may be designed to permit the actuator assembly 20 to draw the pull line 32 in a proximal direction while preventing the pull line 32 from moving in a distal direction.

The means for user actuation is not limited to the handles in the disclosed embodiments and may be any other type of mechanism for actuating the actuator assembly 20 to draw the pull line 32, including mechanisms that use twist knobs, pistol grips and triggers, levers, slides, finger rings, or push buttons. Also, the means for user actuation is not limited to actuation by hand. Actuation may be performed by other parts of the user's body. For example, the means for user actuation may be a foot pedal. Also, the force used to actuate the actuator assembly is not limited to manual force. Actuation may also be machine-driven or machine-assisted. For example, actuation may be driven or assisted by springs, electric motors, or pressurized gas.

In certain embodiments, the means for user actuation may also be adjustable by the user. For example, where the means for actuation are handles, the handle stroke may be adjusted to accommodate hand size or user style or to allow for finer/coarser control. In another example, the means for actuation may include a mechanism for adjusting the amount of force needed to actuate the actuator assembly 20. The force may be adjusted using any conventional mechanism for creating resistance including, for example, a spring mechanism or friction mechanism.

In certain embodiments, the actuator assembly 20 may also comprise a mechanism, using friction for example, to allow the user to freeze one or more components of the actuator assembly as actuation is occurring. Freezing one or more components of the actuator assembly may be used to hold the actuator assembly or the pull line in position. The actuator assembly may also comprise a lock to prevent unintentional actuation. The actuator assembly may also comprise a mechanism for generating audible clicks to indicate that actuation is occurring or has occurred.

The means for drawing the pull line is not limited to the reel or ratchet mechanisms of the embodiments shown herein. In other embodiments, the means for drawing the pull line may be any other type of mechanism that performs the function of drawing the pull line in a proximal direction and/or preventing the pull line from moving in a distal direction. Such other means for drawing the pull line may use any conventional mechanism including those that employ cams or gears.

Figure 2:
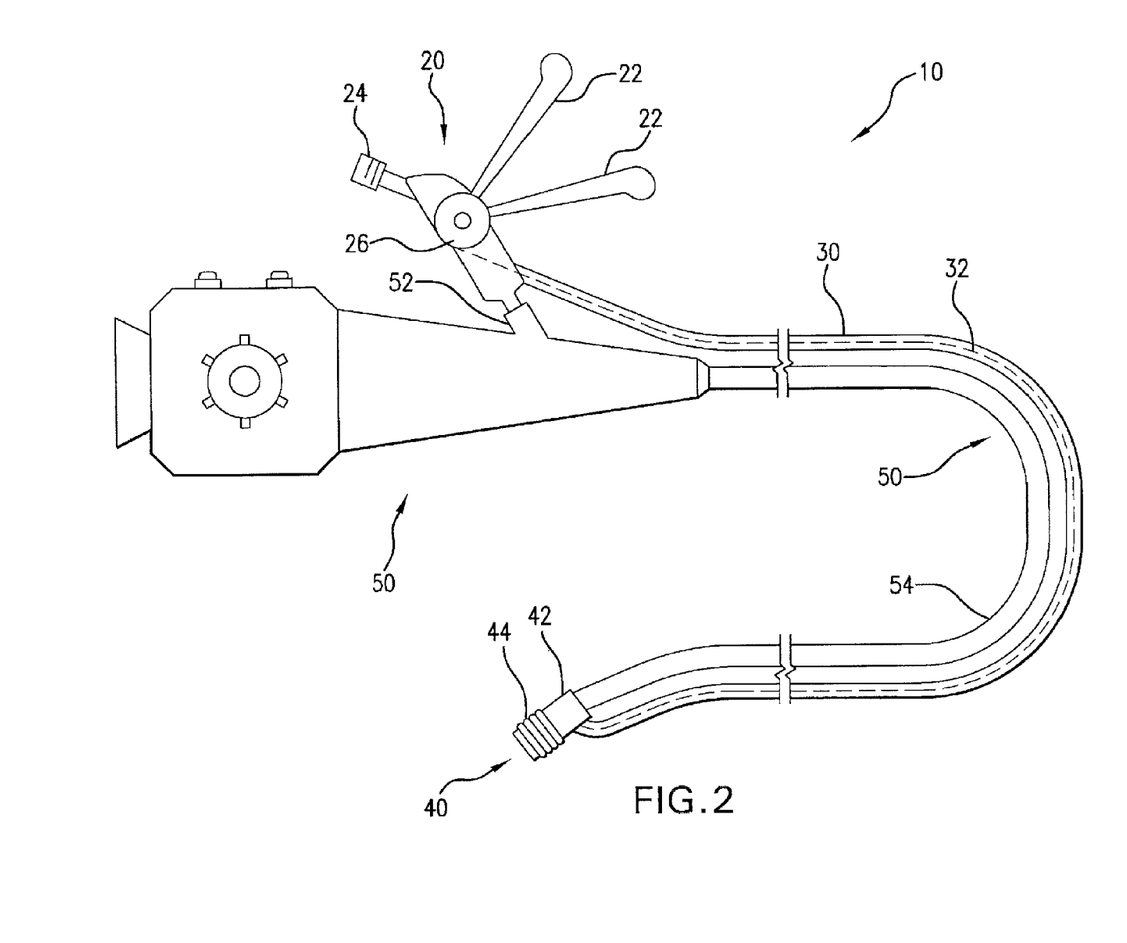
FIG. 2 is a side view of the ligating instrument of FIG. 1 shown alongside an endoscope, with the distal ligating band dispenser and the proximal actuator assembly attached to the endoscope.

Also in the embodiment illustrated in FIG. 2, the actuator assembly 20 includes an adaptor 28 allowing the actuator assembly to be attached to a flush port 52 of the endoscope. In the embodiments shown herein, the actuator assembly 20 includes a flush port 24 which has a lumen continuous with the lumen of the flush port 52 on the endoscope. In alternate embodiments, the proximal actuator assembly 20 may be attached to another part of the endoscope 50. In other alternate embodiments, the proximal actuator assembly 20 may be free of any attachment to the endoscope. In any embodiment, the ligating instrument can be configured to be operated by any person. For example, the ligating instrument may be configured so that one person operates the endoscope while another person operates the ligating instrument. In another example, the ligating instrument may be configured so that the operator of the endoscope also operates the ligating instrument.

The actuator assembly 20 may be placed in various orientations or positions in relation to the endoscope and are not limited to the orientations or positions of the embodiments shown herein. For example, the orientation of the handles 22 can be along any axis, such as perpendicular to the flush port 52.

In operation of the embodiment illustrated in FIG. 2, the user attaches the ligating band dispenser 40 to the distal tip of an endoscope tube 54. The user then unrolls the sleeve 60 to cover the distal end of the ligating instrument 10 and endoscope tube 54. The user inserts the endoscope along with the attached distal end of the ligating instrument 10 into the patient's body cavity, orifice, or lumen and positions the ligating band dispenser 40 adjacent the target site. The proximal end of the ligating instrument 10 remains outside the patient's body. To dispense a ligating band, the user squeezes the actuator handles 22, causing the actuator to draw and ratchet the pull line 32. This drawing of the pull line 32 releases a ligating band from the ligating band dispenser.

The actuator assembly 20 may be calibrated such that a single actuation of the actuator pulls just enough pull line 32 to cause deployment of one ligating band. Then, releasing the actuator sets the mechanism up for the next deployment. Actuating the actuator again pulls just enough pull line 32 to cause deployment of the next ligating band. In this manner, the ligating bands are adapted to be deployed sequentially by sequential actuations of the actuator member.

In certain embodiments, any surface or part of sleeve 60, elongate member 30, or pull line 32 may be coated with a lubricant or be formed of a low friction material. In certain embodiments, the ligating instrument may further comprise a counter indicating the number of ligating bands deployed or the number of ligating bands remaining. In certain embodiments, the ligating instrument may further comprise an indicator, such as a gauge, that indicates that the next ligating band is ready for deployment.

It will be appreciated that the embodiments as described and illustrated in FIGS. 1 through 7 have a number of advantages. First, because the pull line travels outside of the endoscope, there is no need to thread the pull line through a lumen of the endoscope as with prior devices. Thus, setting-up the instrument for use is simplified. Second, the user can mount the instrument onto the endoscope as a single functional unit. There is no need to tie or connect the pull line to the actuator or ligating band dispenser. This also avoids the need to adjust the length of or tension on the pull line before or during use of the instrument. Third, the use of an elongate member through which the pull line travels establishes a fixed length between the ligating band dispenser and the actuator member. In this way, the actuation of the device will not cause the ligating band dispenser and actuator member to move closer relative to one another. Stated another way, the elongate member provides an opposing force allowing drawing of the pull line.

The foregoing embodiments are merely examples of embodiments within the scope of the invention. Other embodiments are possible that incorporate one or more of the features or advantages of the above-described embodiments. This invention thus embraces other embodiments within the scope of the claims.

I claim:

1. A method for using a ligating instrument mounted on an endoscope, comprising:

attaching a ligating band dispenser of the ligating instrument to a distal tip of the endoscope, the ligating band dispenser comprising a support structure and at least one ligating band positioned on the support structure; and deploying the ligating band off of the support structure via an actuator member configured to pull a pull line extending from the ligating band dispenser, an elongate member of the ligating instrument extending from the actuator member to the ligating band dispenser, the elongate member configured to be positioned outside of the endoscope from the ligating band dispenser to the actuator member, an extendable sleeve of the ligating instrument positioned on a distal portion of the ligating instrument, the sleeve configured to be extended proximally such that the sleeve is lengthened proximally along the endoscope and secure at least a portion of the elongate member relative to the outside of the endoscope, wherein the pull line extends through a lumen of the elongate member with a proximal end of the pull line connected to the actuator member and a distal end of the pull line connected to the ligating band dispenser, the pull line entering the ligating band dispenser through an aperture from a position radially outside the ligating band dispenser, wherein an actuation of the actuator member draws the pull line in a proximal direction through the elongate member to deploy the ligating band off of the support structure, and wherein the elongate member establishes a fixed length between the ligating band dispenser and the actuator member.

2. The method of claim 1, wherein the ligating band dispenser is configured to be mounted on the distal tip of the endoscope.

3. The method of claim 1, wherein the extendable sleeve comprises the elongate member.

4. The method of claim 1, wherein the extendable sleeve comprises the pull line.

5. The method of claim 1, wherein the actuator member is configured to be attached to the proximal end of the endoscope.

6. The method of claim 1, wherein the actuator member comprises a ratchet mechanism for user actuation that draws the pull line in a proximal direction while preventing the pull line from moving in a distal direction.

7. The method of claim 6, wherein the ratchet mechanism includes at least one handle.

8. The method of claim 7, wherein the at least one handle is configured to be squeezed to actuate the actuator member to draw the pull line.

9. The method of claim 1, wherein the ligating bands are positioned on the support structure of the ligating band dispenser and wherein the ligating bands are adapted to be deployed sequentially by pulling the pull line.

10. The method of claim 1, wherein the pull wire passes through the support structure so that, when the ligating band dispenser is mounted on the endoscope, the pull wire enters the ligating band dispenser at a position distal to a distal end of the endoscope.

* * * * *